(12) United States Patent
Brock et al.

(10) Patent No.: US 8,508,766 B2
(45) Date of Patent: Aug. 13, 2013

(54) GLOBAL ENTERPRISE PRINTING AND MAILING

(75) Inventors: Thomas J. Brock, Cincinnati, OH (US); Pramod C. Madala, Pickerington, OH (US)

(73) Assignee: Kern International, Inc., Columbus, OH (US)

(*) Notice: Subject to any disclaimer, the term of this patent is extended or adjusted under 35 U.S.C. 154(b) by 1066 days.

(21) Appl. No.: 11/875,624

(22) Filed: Oct. 19, 2007

(65) Prior Publication Data

US 2008/0162240 A1 Jul. 3, 2008

Related U.S. Application Data

(60) Provisional application No. 60/880,923, filed on Jan. 17, 2007.

(51) Int. Cl.
*G06K 15/02* (2006.01)
*G06Q 10/00* (2012.01)

(52) U.S. Cl.
USPC ................ 358/1.15; 358/1.18; 705/8

(58) Field of Classification Search
None
See application file for complete search history.

(56) References Cited

U.S. PATENT DOCUMENTS

| | | | | |
|---|---|---|---|---|
| 5,168,444 A | * | 12/1992 | Cukor et al. | 705/330 |
| 6,959,292 B1 | * | 10/2005 | Pintsov | 705/62 |
| 2002/0012134 A1 | * | 1/2002 | Calaway | 358/1.18 |
| 2002/0184148 A1 | * | 12/2002 | Kahn et al. | 705/40 |
| 2005/0283449 A1 | * | 12/2005 | Jacobson et al. | 705/410 |
| 2006/0020366 A1 | * | 1/2006 | Bloom | 700/226 |
| 2006/0039707 A1 | * | 2/2006 | Mima | 399/23 |
| 2007/0005414 A1 | * | 1/2007 | Connors et al. | 705/9 |

OTHER PUBLICATIONS

PCT International Search Report, mailed Dec. 5, 2008, PCT/US 08/50999, 9 pages.
PCT International Preliminary Report on Patentability, PCT/US 08/50999, mailed Jul. 30, 2009, 7 pages.
Supplementary European Search Report, 08727650.7-2221/2122548, PCT/US2008050999 dated Nov. 20, 2012, 5 pages.

\* cited by examiner

*Primary Examiner* — Gabriel I Garcia
*Assistant Examiner* — Pawandeep Dhingra
(74) *Attorney, Agent, or Firm* — Banner & Witcoff, Ltd.

(57) ABSTRACT

Systems, devices, and methods for global enterprise workflow management are disclosed. The system may include a communications module, memory, and processor for executing a method of managing job information. The system receives job information and uses a model to identify a desirable resource to execute the job. Then the system sends the job information to the identified resource for execution. The resource may send back information associated with the running and/or completion of the job. Various models may be used in identifying a desirable approach, including a cost model, a staffing model, and other models.

19 Claims, 4 Drawing Sheets

GLOBAL ENTERPRISE PRINTING AND MAILING

RELATED APPLICATIONS

This application claims priority to U.S. Provisional Patent Application Ser. No. 60/880,923, filed Jan. 17, 2007, entitled "System and Method for Global Enterprise Printing and Mailing", the entirety of which is herein incorporated by reference.

TECHNICAL FIELD

Aspects of the invention relate generally to industrial processing. More specifically, aspects of the invention provide automating end-to-end processing of document production, assembly, and/or mailing.

BACKGROUND

Today's direct mail house must be flexible in order to respond quickly to ever changing marketing demands from customers. The world is deeply entrenched in the digital age. Digital technologies are here to stay and the mailing industry must maximize efforts to stay with the times. One objective of the mailing industry is to get messages, statements, documents and merchandise to the correct recipient within the prescribed timeframe in order to secure the desired response. To properly address this problem requires a new approach, one that breaks with incremental solutions offering from the past.

In the mailing industry, customers are dealing with a rapidly changing industry, an evolving workforce, and environment of increasing regulation. The industry has several pressures facing each customer, vendor, supplier and 3rd party entities. The largest cost factor or cost element in producing mail is the postage. The industry faces double digit increases that are driving alternative methods by dealing with these extra pressures. This eliminates the cost of paper processing by abolishing the entire paper processing and using technology of the internet and email to reduce the need of the United States Postal Service. Noticeably, electronic document delivery and e-billing provides High Volume Mailing professionals the opportunity to achieve substantial reduction in print and mail costs. Overall electronic document delivery will continue to grow as an importance for all mailers, of all sizes.

The direct mail production process is an extremely complicated process with several incremental steps. Take for example a bank mailing the monthly bank statements to several thousand, or even million, bank customers. The banking records must be extracted from databases, processed into the proper format for a statement, printed out, separated, combined with other mailing items, folded, inserted into mailing envelopes, and sorted by postal codes to achieve mailing discounts. This entire process must be verifiable, so that the bank has reasonable proof that the mailing was properly assembled and mailed to each customer. Achieving efficiency for such processing is difficult.

Today, it is not enough for a company to provide great module technology. Integrated solutions supported by numerous products to maximize postal savings, which are regulated by the United States Postal Service, and other factors are needed to solve the aforementioned issues in the industry.

BRIEF SUMMARY

The following presents a simplified summary of the invention in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

A first aspect of the invention provides a system for providing workflow management. The system includes a communications module, memory, and processor for executing a method of managing job information. The system receives job information and uses a model to identify a desirable resource to execute the job. Then the system sends the job information to the identified resource for execution. The resource may send back information associated with the running and/or completion of the job. Various models may be used in identifying a desirable approach. A cost model, a staffing model, and other models exist in the art and are well-known.

A second aspect of the invention provides a method for workflow management using a plurality of resources located in remote locations in a plurality of countries. The method includes receiving job information, identifying a resource to perform the job, and sending the job information to that resource. In addition, the method steps may be implemented as computer-executable instructions stored in a computer-readable medium.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope of the present invention.

Aspects of the invention provide the ability to manage individual business processes or an entire document factory by providing workflow management with real-time analysis for production print and mail environments. The system allows views of the high-level job tracking that drills down into job details, such as analytical analysis on specific job(s), resource, sorting, house-holding, or employee productivity results. Furthermore, in accordance with various aspects of the invention, secure, real-time visibility provides the current process and status of every job, including the ability to identify those behind schedule and the processes, machines and/or people. Additionally, various aspects of the invention provide promotional content integrated in documents; enables organizations creating dynamic documents from self-service web portals; provides supply solutions that advance beyond just standalone modules or document management; provide software that continues to be a driving force; provide privacy regulations for customers and institutions within the mail world; provide total document integrity; provide an upgrading of legacy systems; and/or provide a focus on flexible systems with all the varied components that comprise a competitive end-to-end workflow.

Figure 1:
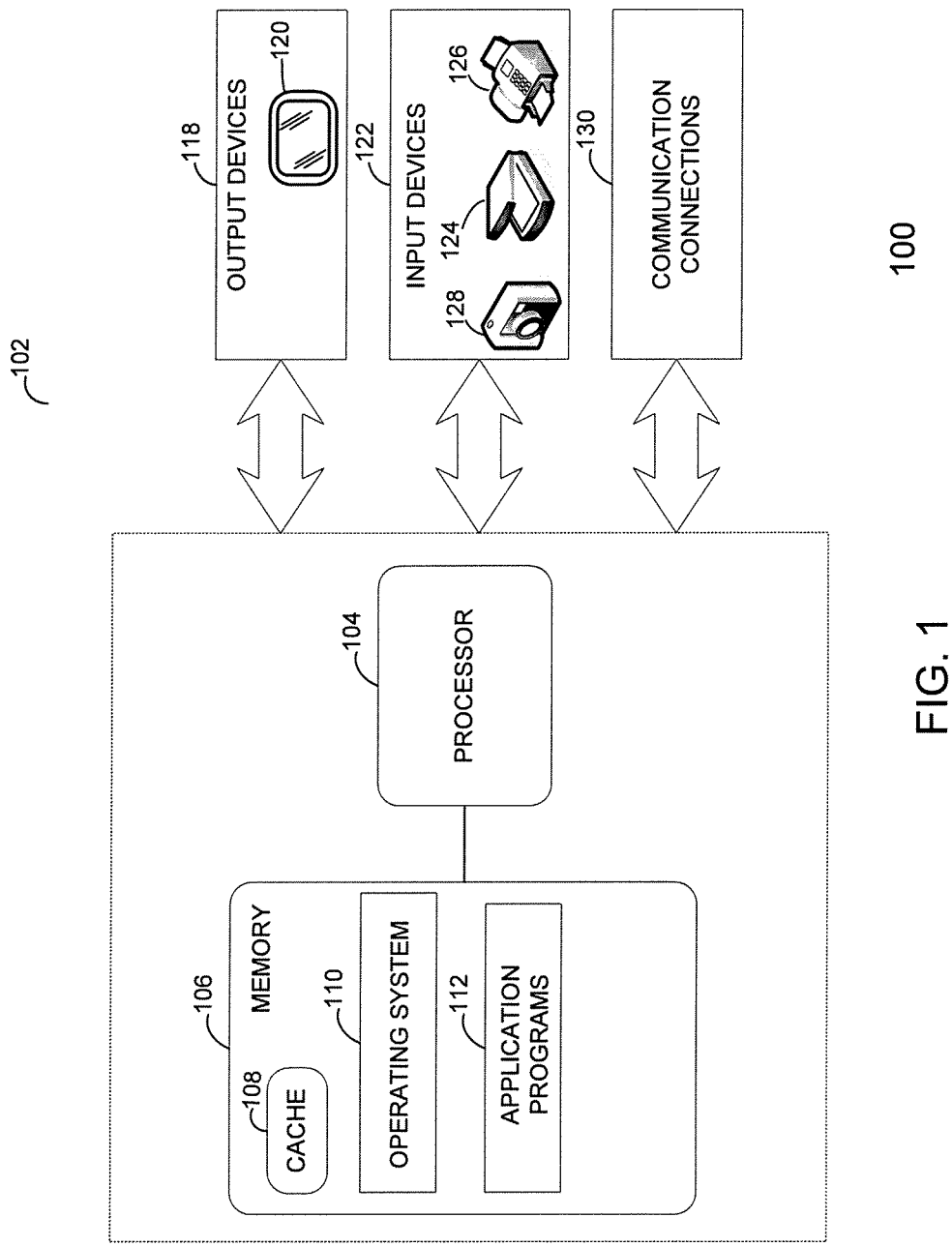
FIG. 1 illustrates a suitable computing system in accordance with aspects of the invention.

An example of an illustrative personal computing system 100 in which various aspects and embodiments of the invention may be implemented is shown in the simplified diagram in FIG. 1. The features of such a device are well-known to those of skill in the art and need not be described at length here. The illustrative system 100 is only one example of a suitable system and is not intended to suggest any limitation as to the scope of use or functionality of the invention. Suitable computing environments for use with the invention include a computing device 102 or system that support interaction with an input devices 122 (e.g., digital camera 128, document scanner 124, multi-function office device 126, etc.), output devices 118 (e.g., visual display device 120), and communication connections 130 (e.g., Ethernet connection, IEEE 802.11, dial-up connection, etc.). The communication connections 130 may be used to allow the computing device 102 to communicate with other devices. With reference to FIG. 1, a computing device 102 commonly includes a memory 106 and a processor 104 (e.g., an Intel microprocessor). The visual display device 120 may be configured to automatically display reporting information in near realtime. The reporting information may be received through the communication connections 130 and automatically passed to the visual display device 120 for near realtime display.

Programs, comprising sets of instructions and associated data, may be stored in the memory 106, from which they can be retrieved and executed by the processing unit 103. Among the programs and program modules stored in the memory 106 are those that comprise or are associated with an operating system 110 as well as application programs 112. Application programs 112, such as a web browser application, Java runtime environment, and others, and an operating system 110 are commonly installed in a computing device 102. The memory 106 may also include a cache 106 to enhance device performance. Computing system 100 includes forms of computer-readable media. Computer-readable media include any available media that can be accessed by the computing device 102. Computer-readable media may comprise storage media and communication media. Storage media include volatile and nonvolatile, removable and non-removable media implemented in any method or technology for storage of information such as computer-readable instructions, object code, data structures, program modules, or other data. Communication media include any information delivery media and typically embody data in a modulated data signal such as a carrier wave or other transport mechanism.

Aspects of the inventive methods may be embodied as computer readable instructions stored on a computer readable medium such as a floppy disk, CD-ROM, removable storage device, hard disk, system memory, or other data storage medium. FIG. 1 illustrates a block diagram of a computer readable medium 106 that may be used in accordance with one or more of the above described embodiments. The computer readable medium 106 stores computer executable components, or the numerous software modules described below. More or fewer software modules may alternatively be used. Each component may be an executable program, a data link library, a configuration file, a database, a graphical image, a binary data file, a text data file, an object file, a source code file, or the like. As will be appreciated by one of skill in the art, the functionality of the software modules may be combined or distributed as desired in various embodiments. When one or more computer processors (e.g., processing units) execute one or more of the software modules, the software modules interact to cause one or more computer systems to perform according to the teachings of the present invention.

Figure 3:
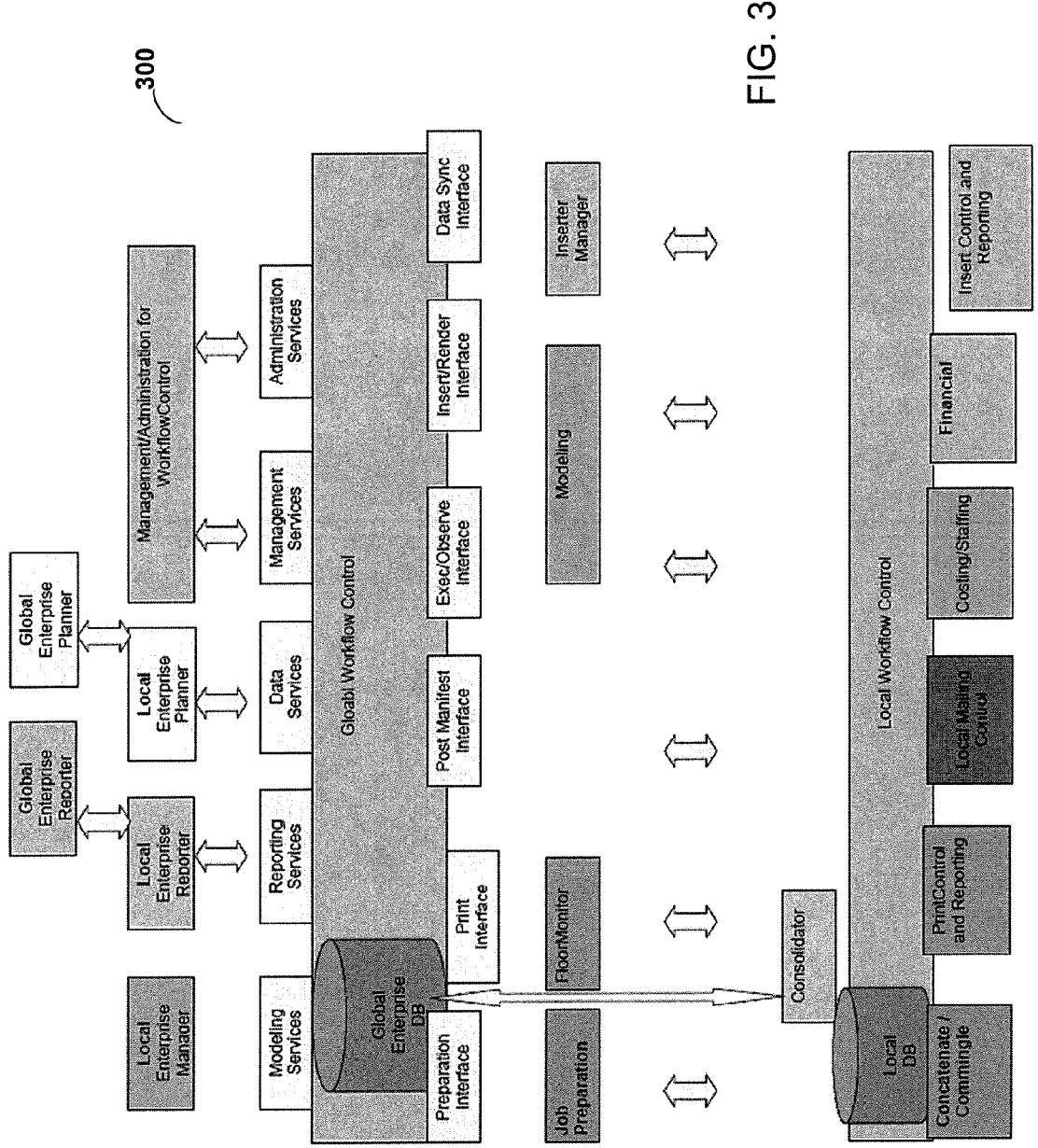
FIG. 3 illustrates a global enterprise printing and mailing model in accordance with aspects of the invention.

Referring to FIG. 3, the global enterprise printing and mailing model 300 is a process that is designed around the printing and mailing operations of any entity in the print and mail operations industry. This model allows global business entities to build staffing, financial, cost models, concatenate and/or commingle jobs to attain low cost per piece and maximize capacity. This concept also provides a global work flow view connecting all the national business entities and international business entities into one model. The concept is based on building several modules into a global model. Such modules and their core functionality are highlighted below.

One such module is the print control and reporting module, and local mailing control module. Numerous features of these modules in accordance with aspects of the invention are disclosed in U.S. Provisional Patent Application Ser. No. 60/880,923 (filed Jan. 17, 2007), the entirety of which has already been incorporated by reference above, including, but not limited to, in the sections labeled accordingly, including the corresponding flow chart diagrams. Those sections list various method steps and approaches associated with aspects of such modules.

In the global enterprise printing and mailing model 300, a scanning device 124 (e.g., a bar code scanning device) may be located at each of the plurality of resources configured to scan a barcode on the printing device. For example, a different barcode may correspond to the various functions and inputs that a maintenance technician or device operator may wish to input/record about the system. The technician may scan a barcode designated for repairs each time a printing machine has a malfunction and requires repair. In some examples, there may be a barcode for start repair and a different one for stop repair. As such, information may be collected and stored regarding the system that may be used for model information.

Another module in the global enterprise printing and mailing model is the costing and staffing module. Numerous features of this module in accordance with aspects of the invention are disclosed in U.S. Provisional Patent Application Ser. No. 60/880,923 (filed Jan. 17, 2007), the entirety of which has already been incorporated by reference above, including, but not limited to, in the section labeled "Costing/Staffing" which includes the corresponding flow chart diagrams. That section, which has already been incorporated by reference in this application, lists various method steps and approaches associated with aspects of such a module.

In the global enterprise printing and mailing model 300, the costing and staffing module may use model information stored in memory (e.g., a global enterprise database or a local database) to identify a desirable facility or resource located anywhere worldwide to utilize. The model information may comprise information about cost of materials (e.g., envelopes, inserts, paper, consumables, ink, etc.), cost of print image, cost of labor (e.g., cost of staff required to run various systems such as upstream software, printers, inserters, and cost of supervisors for the staff), postal cost, hard costs (e.g., building costs, utilities, any internal billing costs, etc.), history of cost, holiday schedule, vacation schedule, and production schedule. One skilled in the art will appreciate that other factors may be useful to monitor and/or record for purposes of creating a model, and the invention is not so limited to the aforementioned list of non-exhaustive factors.

The model information may be used to identify a desirable facility based on various business rules embodied in various models. For example, under a cost model approach, collected heuristic cost information is considered while predicting future cost per piece. In addition, information about the hard costs for a particular site (e.g., resource/facility) is considered. Moreover, the cost of paper and other materials is considered in light of the paper type and weight (e.g., 18 lb paper, 20 lb paper, 22 lb paper, etc.) used. Under a different model, the staffing model, collected heuristic schedule information is considered while predicting future schedules. In addition, information about how many employees a particular type of machine (e.g., printer device, inserter device, etc.) requires is considered. Moreover, the forecasted month end, quarter end, and year end volumes are considered. Finally, under yet another model the approach may be based on a maximizing utilization of the plurality of resources available to the workflow. For example, concatenate and commingle module may use business rules to sort based on achieving low cost per piece, or based on the international guidelines, or based on maximizing machine utilization. Likewise, information collected will be used to drive the decision process under the business rules. One skilled in the art will appreciate that various statistical methods may be used to construct each model with its associated business rules.

In one example, a desirable facility may be identified by attributing equal weight to cost savings and machine utilization. In such an example, each resource site's cost per piece may be calculated using numerous factors (e.g., cost of materials, cost of equipment, hard costs, etc.) and compared to a benchmark cost value. For example, site A may be found to cost $0.15 per piece, while site B costs $0.17 per piece. Assuming a benchmark cost of $0.15 per piece, site A would be assigned a higher rank (e.g., a value of 1.0) than site B (e.g., a value of 0.9). In addition, the utilization rating of each site may also be considered. Assuming site A has a machine utilization of 1.0 (i.e., where 0.5 represents 50% utilization) and site B has a machine utilization of 1.0 (i.e., where 1.0 represent 100% utilization), then site A may have a higher rank in this line-up than site B. Therefore, it may be identified that site A is the desirable resource to use since it has a lower cost per piece and has excess machine capacity to provide. One skilled in the art will appreciate that the weights attributed to the various considerations may be adjusted depending on a client's particular objectives.

Another module in the global enterprise printing and mailing model is the concatenating and commingling module. Numerous features of this module in accordance with aspects of the invention are disclosed in U.S. Provisional Patent Application Ser. No. 60/880,923 (filed Jan. 17, 2007), the entirety of which has already been incorporated by reference above, including, but not limited to, in the section labeled "Concatenating and Commingling" which includes the corresponding flow chart diagrams. That section, which has already been incorporated by reference in this application, lists various method steps and approaches associated with aspects of such a module.

Other modules in the global enterprise printing and mailing model include: the financial module, the insert control and reporting module, the job preparation module, the floor monitoring module, the modeling module, the inserter manager module, the enterprise manager module, the enterprise report module, the enterprise planner module, and the management/administration of work flow control module. Numerous features of these modules in accordance with aspects of the invention are disclosed in U.S. Provisional Patent Application Ser. No. 60/880,923 (filed Jan. 17, 2007), the entirety of which has already been incorporated by reference above, including, but not limited to, in the sections labeled accordingly, including the corresponding flow chart diagrams. Those sections list various method steps and approaches associated with aspects of such modules.

In addition, numerous features of the systems and steps of the methods in accordance with aspects of the invention are disclosed in U.S. Provisional Patent Application Ser. No. 60/880,923 (filed Jan. 17, 2007), the entirety of which has already been incorporated by reference above, including, but not limited to, in the table labeled "BRD Response Summary/Gap Analysis." That table, which has already been incorporated by reference in this application, lists various business rules associated with aspects of the invention and various functionality that may be implemented to address application requirements and associated business rules. One of ordinary skill in the art will appreciate that where words such as "need" or "must" have been used in the aforementioned U.S. Provisional Patent Application, they shall not be construed to limit the invention.

Figure 2:
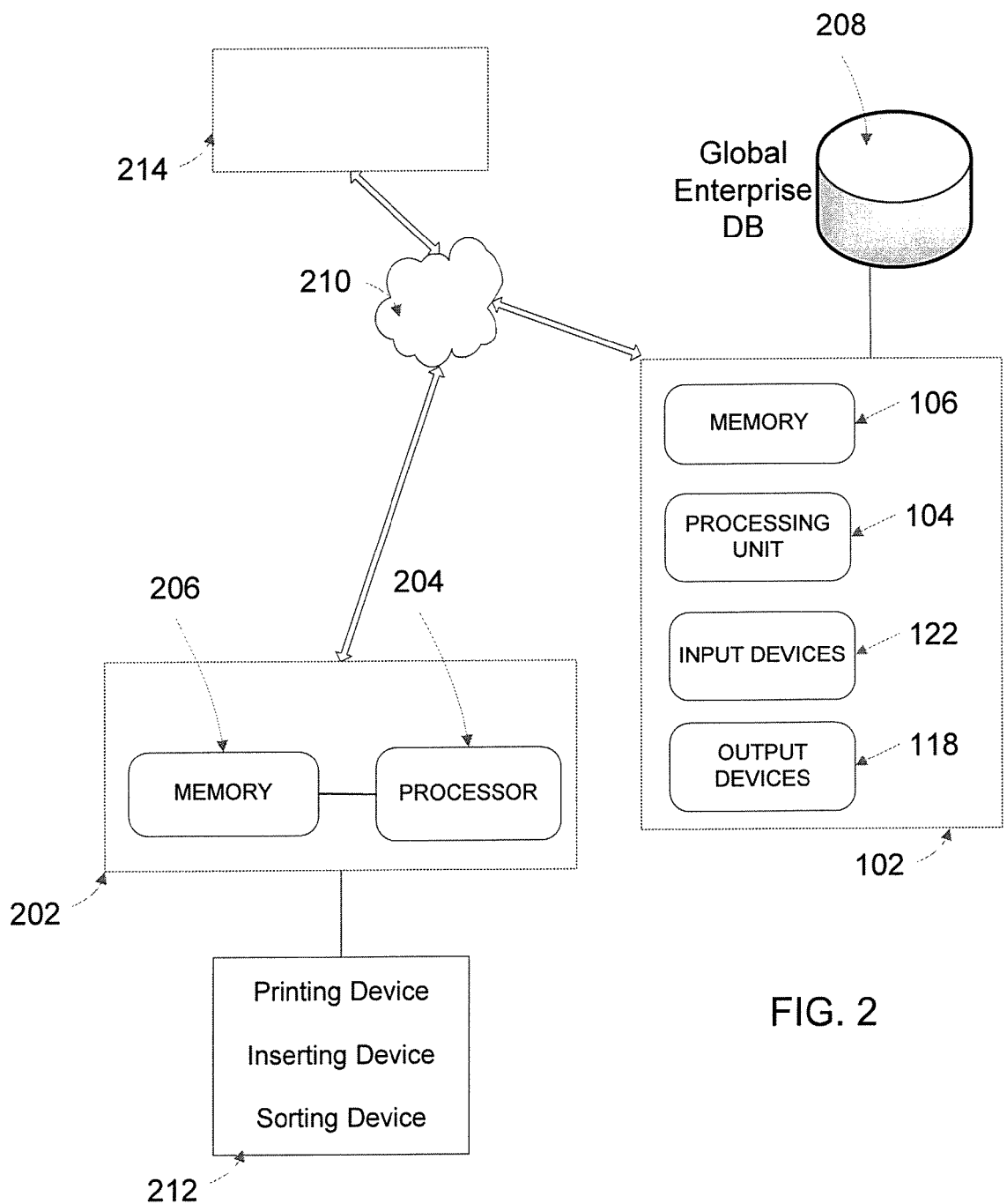
FIG. 2 illustrates a simplified, illustrative operating environment for implementing various aspects and embodiments of the invention.

FIG. 2 depicts a simplified, illustrative operating environment for implementing various aspects and embodiments of the invention. The illustrative operating environment in FIG. 2 is only one example of a suitable operating scenario and is not intended to suggest any limitation as to the scope of use or functionality of the invention.

In the global enterprise printing and mailing model 300, resources may be spread across the globe. For example, resources 214, 202, and 102 may be located in different countries in remote locations. Each resource may contain a computing device similar to the computing system 100 of FIG. 1. The computing system 202 may contain a memory 206 and processor 204. In addition, a data store 208 may be in communication with a computing system 102 to store information, such as job information (e.g., information associated with a print and/or mail job) and model information.

In one example, a resource 202 with a computing device may receive job information from a computing system 102 controlling the global workflow. The computing device 202 may process the job information and send print image data to various devices 212 (e.g., printing device, inserting device, and/or sorting device) to perform the document functions. In addition, any additional information (e.g., information collected from a handheld barcode scanner at devices 212) may be collected and sent, along with other operating information, to computing system 102 for storage as model information in global enterprise database 208 (or data store).

One skilled in the art will appreciate that the network 210 may be any of the Internet, wide area network (WAN), local area network (LAN), wireless LAN (e.g., a LAN using IEEE 802.11, a Bluetooth network, etc.) or any other telecommunications network (e.g., satellite, cable, dial-up, etc.) that permits communication between remote computing systems. Furthermore, the network 210 may include wired and/or wireless communication.

The computing system 102 may be comprised of a memory 106 storing computer-executable instructions and a processor 104 for executing the instructions. The instructions may direct the computing device 102 to perform numerous functions, including various functions described in FIG. 4 and throughout this disclosure. One skilled in the art will appreciate that the computing devices as depicted in FIG. 2 are not limited to a single machine or device. Rather, the term refers to any system of computers and/or devices (e.g., firewalls, routers, caching systems, proxy servers, etc.) that may be used to provide access to services and features available for access in the global enterprise model 300. As such, different reference to the term performing particular steps does not require that the same machine/device perform all the steps.

Figure 4:
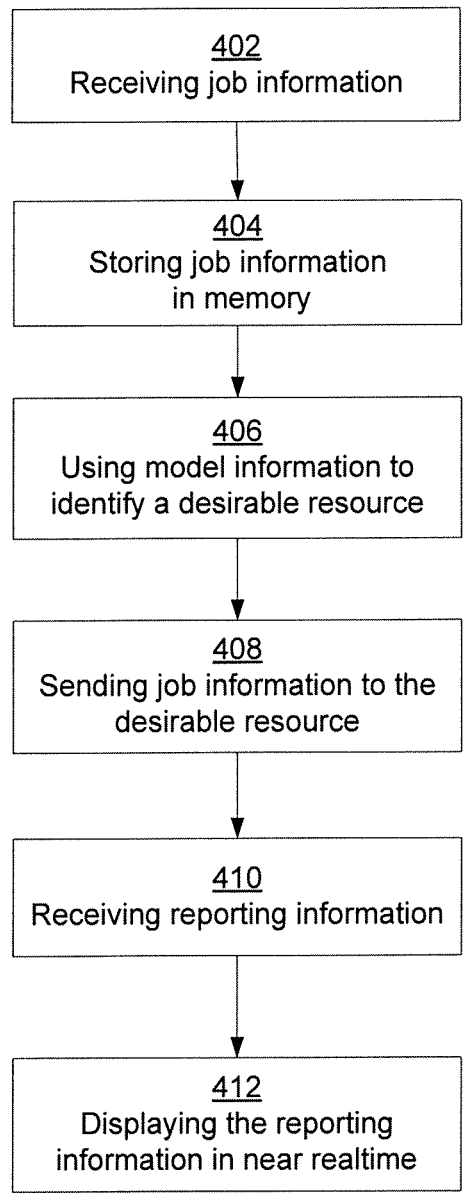
FIG. 4 illustrates a flowchart showing a method in accordance with aspects of the invention.

Referring to FIG. 4, a method of workflow management using a plurality of resources located in remote locations in a plurality of countries is represented. In step 402, job information is received from a remote location. In step 404, the job information is stored in computer memory. In step 406, using model information stored in the memory, a desirable resource is identified to execute a job corresponding to the job information. In step 408, at least part of the job information is sent to the desirable resource. The desirable resource may include a printing device, inserting device, and sorting device 212. In step 410, reporting information is received from the desirable resource. The reporting information is associated with the job information and may include data collected at the resource facility by maintenance technicians and other employees operating the devices 212. For example, this may include print device monitoring information entered using a scanning device. The print device monitoring information may be stored in memory as part of the model information. In step 412, the reporting information is displayed on a visual display device in a near realtime manner. The visual display may be use the floor monitor module disclosed in U.S. Provisional Patent Application Ser. No. 60/880,923 (filed Jan. 17, 2007), the entirety of which has already been incorporated by reference above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A system for providing workflow management, comprising:
    a communications module configured to communicate with a plurality of resources located in a plurality of different countries, where the plurality of resources comprise an inserting device, sorting device, and printing device;
    a memory configured to store job information and model information comprising cost of materials, cost of print image, cost of labor, postal cost, hard costs, and history of cost, wherein the model information identifies a utilization rating of each of the plurality of resources located in different countries and a postal cost based on paper weight, wherein the utilization rating corresponds to a resource's excess available capacity, and wherein the memory comprising non-volatile memory for storing computer-executable instructions; and
    a processor configured to execute the computer-executable instructions to perform a method comprising:
        receiving the job information from a remote location, wherein the job information includes attribute of the paper weight;
        automatically determining, by the processor using the model information, a first resource of the plurality of resources with a higher utilization ranking than a second resource of the plurality of resources located in remote locations, wherein the resources are located in remote location in different countries;
        sending the job information to the first resource in the different country to cause the first resource to execute the job corresponding to the job information, wherein executing the job comprises:
            printing, using the printing device at the first resource, at least the job corresponding to the job information; and
            causing the printed job to be mailed; and
        receiving reporting information from the first resource, the reporting information being associated with the job information.

2. The system of claim 1, where the remote location and a location of the desirable resource are in different countries.

3. The system of claim 1, where the job information comprises account number, address, zip code, and paper size.

4. The system of claim 1, comprising:
    a visual display device located at each of the plurality of resources configured to display the reporting information.

5. The system of claim 4, where the reporting information is automatically displayed on the visual display device in near realtime.

6. The system of claim 1, comprising:
    a barcode scanning device located at each of the plurality of resources configured to scan a barcode on the printing device.

7. The system of claim 1, where the model information further comprises holiday schedule, vacation schedule, and production schedule.

8. The system of claim 1, where the model information is based on a cost model, and the system further comprises a local mailing control module configured to use the model information to identify the desirable resource to execute the job corresponding to the job information.

9. The system of claim 7, where the model information is based on a staffing model.

10. The system of claim 1, where the model information is based on maximizing utilization of the plurality of resources.

11. A method of workflow management using a plurality of resources located in remote locations in a plurality of countries, wherein the plurality of resources comprises an inserting device, sorting device, and printing device, the method comprising:
    receiving job information from a remote location;
    storing the job information in a memory, wherein the job information includes attribute of paper weight;
    using model information stored in the memory to automatically identify a desirable resource to execute a job corresponding to the job information, wherein the model information comprises at least one of cost of materials, cost of print image, cost of labor, postal cost, hard costs, and history of cost, and wherein the model information identifies a desirable resource from among the plurality of resources based on its higher rankings for machine utilization and material cost savings, wherein the machine utilization corresponds to a resource's used capacity, wherein the plurality of resources are located in remote location in different countries;
    sending at least part of the job information to the desirable resource, where the desirable resource comprises a printing device and an inserting device;
    receiving reporting information from the desirable resource indicating that the desirable resource has printed at least the job information using the printing device and caused the printed job to be mailed and
    displaying the reporting information on a visual display device in a near realtime manner.

12. The method of claim 11, where the job information comprises account number, address, and paper size.

13. The method of claim 11, further comprising:
receiving print device monitoring information entered using a scanning device, the print device monitoring information being stored in the memory as part of the model information.

14. The method of claim 11, where the desirable resource further comprises a sorting device.

15. The method of claim 11, where the model information comprises cost of materials, cost of labor, postal cost, and hard costs.

16. The method of claim 15, where the model information is based on a cost model.

17. The method of claim 11, where the model information is based on a staffing model.

18. A non-transitory computer-readable storage medium storing computer-executable instructions which, when executed by a processor, cause the processor to perform a method comprising:
receiving job information from a remote location;
storing the job information in a memory, wherein the job information includes attribute of paper weight;
using model information stored in the memory to automatically identify a desirable resource from a plurality of resources located in a plurality of countries to execute a job corresponding to the job information, wherein the plurality of resources comprises an inserting device, sorting device, and printing device, wherein the model information comprises at least one of cost of materials, cost of print image, cost of labor, postal cost, hard costs, and history of cost, and wherein the model information identifies a desirable resource from among the plurality of resources based on its higher rankings for machine utilization and material cost savings, wherein the machine utilization corresponds to a resource's used capacity, wherein the plurality of resources are located in remote location in different countries;
sending at least part of the job information to the desirable resource, where the desirable resource comprises a printing device and an inserting device; and
receiving reporting information from the desirable resource indicating that the desirable resource has printed at least the job information using the printing device, the reporting information being associated with the job information.

19. The computer-readable storage medium of claim 18, where the model information comprises cost of materials, cost of labor, postal cost, and hard costs, and the desirable resource is identified based on a cost model.

* * * * *